United States Patent
Feng

(10) Patent No.: US 9,897,791 B2
(45) Date of Patent: Feb. 20, 2018

(54) OPTICAL SCANNING SYSTEMS FOR IN SITU GENETIC ANALYSIS

(71) Applicant: Illumina, Inc., San Diego, CA (US)

(72) Inventor: Wenyi Feng, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 183 days.

(21) Appl. No.: 14/884,631

(22) Filed: Oct. 15, 2015

(65) Prior Publication Data
US 2016/0109693 A1    Apr. 21, 2016

Related U.S. Application Data

(60) Provisional application No. 62/064,881, filed on Oct. 16, 2014.

(51) Int. Cl.
*G02B 21/36* (2006.01)
*G02B 21/00* (2006.01)
(Continued)

(52) U.S. Cl.
CPC ......... *G02B 21/361* (2013.01); *G02B 21/006* (2013.01); *G02B 21/008* (2013.01); *G02B 21/0076* (2013.01); *G02B 21/362* (2013.01); *H04N 5/2253* (2013.01); *H04N 5/2254* (2013.01); *H04N 5/232* (2013.01)

(58) Field of Classification Search
CPC .............. G02B 21/006; G02B 21/0076; G02B 21/008; G02B 21/361; G02B 21/362; H04N 5/2253; H04N 5/2254; H04N 5/232
See application file for complete search history.

(56) References Cited

U.S. PATENT DOCUMENTS

| | | | |
|---|---|---|---|
| 7,205,549 B2 * | 4/2007 | Yoshida | G01N 21/8806 250/307 |
| 2001/0012069 A1 * | 8/2001 | Derndinger | G02B 21/0036 348/295 |

(Continued)

FOREIGN PATENT DOCUMENTS

DE    19714221    10/1998

OTHER PUBLICATIONS

Nie et al, Thirty two-stage CMOS TDI Image sensor with on-chip analog accululator, 2013.*

(Continued)

*Primary Examiner* — Shan Elahi
(74) *Attorney, Agent, or Firm* — Illumina, Inc.

(57) ABSTRACT

Presented herein are systems and methods for performing sequencing, including fluorescence in situ sequencing. In one embodiment, a confocal time delay and integration (TDI) line scan imaging system may include various pinhole and/or slit aperture mechanisms in front of the image sensor. The system may also include structures with focusing strips on a substrate in contact with the tissue sample to be imaged. Alternatively, these strips may be cut into the tissue sample. The system may also include configurations and methods of placing a tissue sample inside a reaction chamber of a flow cell during the assembly of the flow cell and then performing chemistry operations on the tissue sample. The flow cells may use an open container for performing chemistry operations on the tissue sample.

27 Claims, 17 Drawing Sheets

(51) Int. Cl.
*H04N 5/225* (2006.01)
*H04N 5/232* (2006.01)

(56) References Cited

U.S. PATENT DOCUMENTS

| | | | |
|---|---|---|---|
| 2004/0001618 A1* | 1/2004 | Johnson | G01N 15/14 382/131 |
| 2014/0152797 A1* | 6/2014 | Mitsuhiro | G01N 21/8806 348/79 |
| 2015/0234178 A1* | 8/2015 | Azuma | G02B 26/0875 359/201.2 |

OTHER PUBLICATIONS

Lepage et al, Time-Delay-Integration architectures in CMOS Image sensors, Nov. 2009.*

* cited by examiner

A-A

OPTICAL SCANNING SYSTEMS FOR IN SITU GENETIC ANALYSIS

CROSS REFERENCE TO RELATED APPLICATIONS

Any and all applications for which a foreign or domestic priority claim is identified in the Application Data Sheet as filed with the present application are hereby incorporated by reference under 37 CFR 1.57.

BACKGROUND

In a conventional (i.e., wide-field) fluorescence microscope, the entire specimen is flooded evenly in light from a light source. All parts of the specimen in the optical path are excited at the same time and the resulting fluorescence is detected by the microscope's photodetector or camera including a large unfocused background part. In contrast, a confocal microscope uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required.

A drawback of some photoluminescence-based scanning instruments (or imaging systems) that are used in current fluorescence-based sequencing-by-synthesis (SBS) systems is that they have poor confocality (i.e., are semi-confocal at best). These semi-confocal imaging systems have a low signal-to-noise (S/N ratio) and therefore are not adequate to eliminate out-of-focus features in specimens. Further, current dithering focus tracking methods are unable to maintain focus during imaging. Therefore, new approaches are needed for imaging (or scanning) in photoluminescence-based SBS systems.

BRIEF SUMMARY

Various implementations of systems, methods and devices within the scope of the appended claims each have several aspects, no single one of which is solely responsible for the desirable attributes described herein. Without limiting the scope of the appended claims, some prominent features are described herein.

Systems and methods for performing fluorescence in situ sequencing are disclosed. Namely, one embodiment provided herein is a confocal time delay and integration (TDI) line scan imaging system that has high S/N ratio and high confocality for producing high resolution images of a sample. In one example, the confocal TDI line scan imaging system comprises various pinhole and/or slit aperture mechanisms in front of the image sensor, wherein the various pinhole and/or slit aperture mechanisms are used to reject out-of-focus light. In another example, the confocal TDI line scan imaging system comprises the various pinhole and/or slit aperture mechanisms in an intermediate image plane conjugating to the image sensor.

Also provided herein are structures that comprise focus tracking features that can be used to maintain focus during imaging. In one example, provided are various configurations of focusing strips on a substrate in contact with the tissue sample to be imaged. In another example, strips are cut into the tissue sample, thereby providing exposed strips of substrate that can be used as focus tracking features.

Also provided herein are flow cells for and methods of processing tissue samples in a flow cell. Namely, provided herein are various configurations and methods of placing the tissue sample inside the reaction chamber of a flow cell during the assembly of the flow cell and then performing chemistry operations on the tissue sample.

Also provided herein are flow cells that use an open container for performing chemistry operations on the tissue sample. In one example, a substantially "dry" imaging process can be used. In another example, a liquid-immersion imaging process can be used.

The details of one or more embodiments are set forth in the accompanying drawings and the description below. Other features, objects, and advantages will be apparent from the description and drawings, and from the claims.

Figure 1:
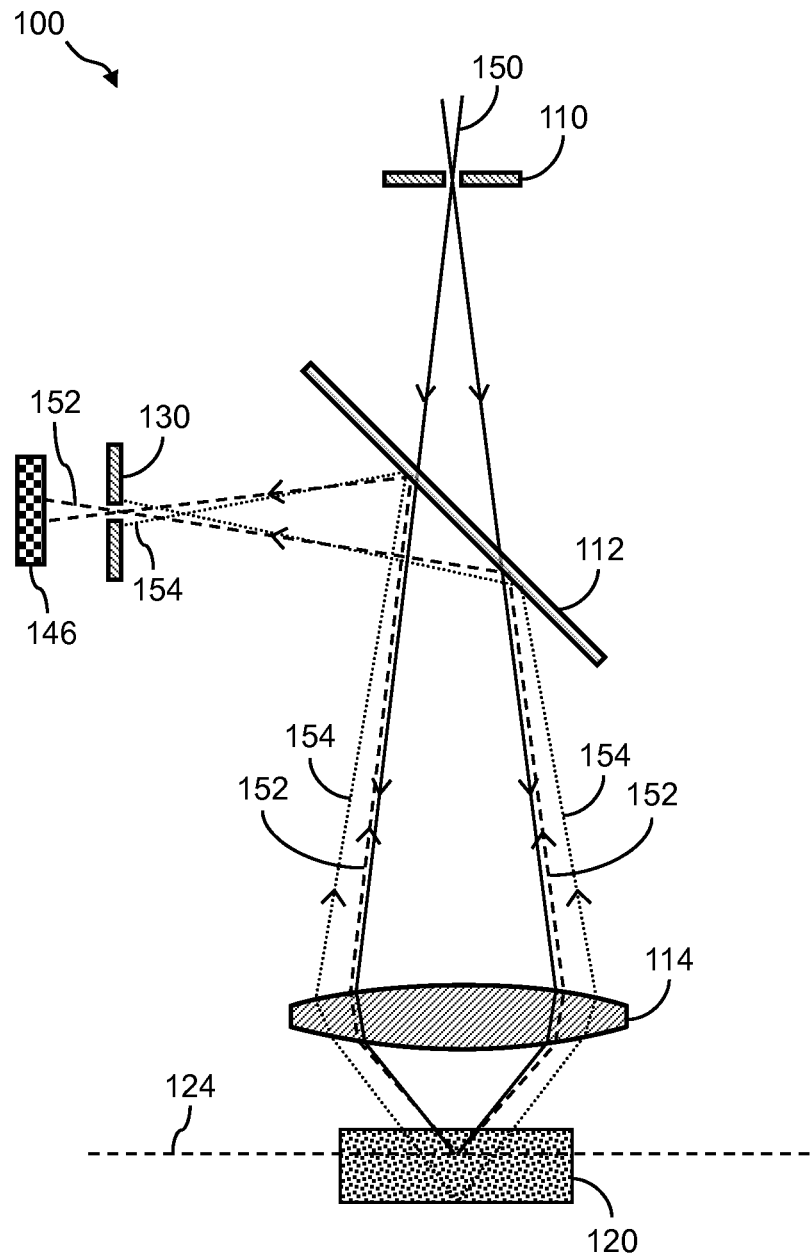
FIG. 1 illustrates a side view of an example of a confocal imaging system according to one embodiment.

The various features illustrated in the drawings may not be drawn to scale. Accordingly, the dimensions of the various features may be arbitrarily expanded or reduced for clarity. In addition, some of the drawings may not depict all of the components of a given system, method or device.

DETAILED DESCRIPTION

The detailed description set forth below in connection with the appended drawings is intended as a description of exemplary embodiments of the invention and is not intended to represent the only embodiments in which the invention may be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the invention. In some instances, some devices are shown in block diagram form.

Sequencing

Systems and methods described herein can be used in conjunction with a variety of nucleic acid sequencing techniques. These sequencing techniques include, but are not limited to, in situ sequencing techniques for reading sequence information from nucleic acids directly from cells or tissue (Lee, Je Hyuk, et al. "Fluorescent in situ sequencing (FISSEQ) of RNA for gene expression profiling in intact cells and tissues." Nature protocols 10.3 (2015): 442-458; Lee, Je Hyuk, et al. "Highly multiplexed subcellular RNA sequencing in situ." Science 343.6177 (2014): 1360-1363; and Mitra, Robi D., et al. "Fluorescent in situ sequencing on polymerase colonies." Analytical biochemistry 320.1 (2003): 55-65, the disclosures of which are incorporated herein by reference in their entireties). Particularly applicable techniques are those wherein nucleic acids are present at fixed locations on a substrate (e.g. an array or tissue sample) such that their relative positions do not change and wherein the substrate is repeatedly imaged. For example, the nucleic acids can be attached to the substrate covalently or non-covalently. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the systems and methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed at Illumina, Inc.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed at Illumina, Inc.

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be located on a substrate (e.g. features in an array) and the substrate can be imaged to capture the chemiluminscent signals that are produced due to incorporation of a nucleotides at the locations on the substrate where the nucleic acids are located. An image can be obtained after the substrate is treated with a particular nucleotide type (e.g. A, T, C or G). Images obtained after addition of each nucleotide type will differ with regard to which features on the substrate are detected. These differences in the image reflect the different sequence content of the features on the substrate. However, the relative locations of each feature will remain unchanged in the images. The images can be stored, processed and analyzed using the methods set forth herein. For example, images obtained after treatment of the substrate with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or degradable (e.g. photo bleachable) dye label as described, for example, in WO 04/018497 and U.S. Pat. No. 7,057,026, the disclosures of which are incorporated herein by reference. This approach is being commercialized by Illumina Inc., and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into nucleic acid features on arrays or other substrates. In particular embodiments, each cycle involves simultaneous delivery of four different nucleotide types to the substrate and each nucleotide type has a spectrally distinct label. Four images can then be obtained, each using a detection channel that is selective for one of the four different labels. Alternatively, different nucleotide types can be added sequentially and an image of the substrate can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. No. 7,427,673, and U.S. Pat. No. 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-channel sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of nucleic acid features on a substrate (e.g. array or tissue) with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. No. 7,329,492 and U.S. Pat. No. 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589A1; US 2010/0137143A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above nucleic acid sequencing methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher. Other substrates can include nucleic acid features at similar density ranges.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Pat. No. 8,951,781, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeg™ platform (Illumina, Inc., San Diego, Calif.) and devices described in U.S. Pat. No. 8,951,781, which is incorporated herein by reference.

Confocal Imaging System

Confocal TDI line scan imaging systems that have high S/N ratio and high confocality for producing high resolution images as described herein below with reference to FIGS. 1, 2, 3, 4A, 4B, 5A, and 5B.

In certain embodiments, confocal TDI line scan imaging systems include a detector array that achieves confocality in the scanning axis by restricting the scan-axis dimension of the detector array. For example, confocality may be achieved in a single axis of a detector array such that confocality only occurs in that dimension. Thus, in contrast to typical confocal systems where confocality is achieved in two dimensions, confocal TDI line scan imaging systems can be configured such that confocality is not achieved in more than one dimension.

Confocal TDI line scan imaging systems may also be configured to sequentially detect different portions of a sample by different subsets of elements of a detector array, wherein transfer of charge between the subsets of elements proceeds at a rate synchronized with and in the same direction as the apparent motion of the sample being imaged. For example, confocal TDI line scan imaging systems may scan a sample such that a frame transfer device produces a continuous video image of the sample by means of a stack of linear arrays aligned with and synchronized to the apparent movement of the sample, whereby as the image moves from one line to the next, the stored charge moves along with it. Accumulation of charge can integrate during the entire time required for the row of charge to move from one end of the detector to the serial register (or to the storage area of the device, in the case of a frame transfer CCD). Exemplary Confocal TDI line scan imaging systems are described, for example, in U.S. Pat. No. 7,329,860, which is incorporated herein by reference. FIG. 1 illustrates a side view of an example of a confocal imaging system 100 according to certain embodiments of the invention. Confocal imaging system 100 is, for example, a TDI line scan imaging system that has high S/N ratio and high confocality for producing high resolution images.

The presently disclosed confocal imaging system 100 is suitable for use in, for example, photoluminescence-based scanning instruments (or imaging systems) that are used in fluorescence-based SBS systems.

Confocal imaging system 100 comprises a light source aperture 110, an optical beam splitter 112, a lens 114, a sensor aperture mechanism 130, and a TDI image sensor 146. In confocal imaging system 100, a tissue sample 120 is arranged at a focal plane 124 with respect to lens 114. Tissue sample 120 is the sample tissue to be imaged (or scanned) in, for example, an SBS process.

Sensor aperture mechanism 130 is positioned in an optically conjugate plane in front of TDI image sensor 146 to substantially eliminate out-of-focus signal and provide high confocality. Namely, various embodiments of sensor aperture mechanism 130 include pinholes or slits to substantially eliminate out-of-focus signal. The substantial elimination of out-of-focus signal may be technically advantageous when used for in situ sequencing techniques.

As introduced above, in situ sequencing techniques involve reading sequence information from nucleic acids directly from tissue without extracting nucleic acid from the tissue. This can be contrasted with sequencing techniques involving extracting nucleic acid from tissue in order to read the sequence information from the extracted nucleic acid. Therefore, sequencing in situ may provide a deeper understanding of the relationship between a cell's genotype or gene expression and its morphology and local environment.

By calibrating the sensor aperture mechanism 130 to substantially eliminate out-of-focus signal, only the light from a focal plane just focused at a slit of the sensor aperture mechanism 130 is allowed reach the image detector. Therefore, optical resolution of nucleic acid within a specific depth of tissue (from the focal plane just focused at the slit) may be increased relative to systems that do not substantially eliminate out-of-focus signals. This type of optical sectioning simulates removing unwanted portions of tissue away (without removing any tissue). Additionally, the width of the slit (or size of a pinhole) may be correlated with resolution, with smaller slit widths (or smaller pinholes) providing increased resolution.

In operation, a light source 150 passes through light source aperture 110, then through optical beam splitter 112, then through lens 114 and impinges on tissue sample 120 at focal plane 124. Light source 150 is the excitation light source for illuminating tissue sample 120 during the imaging (or scanning) process. In so doing, tissue sample 120 emits certain in-focus fluorescent light 152 with respect to sensor aperture mechanism 130 and TDI image sensor 146 as well as certain out-of-focus fluorescent light 154. In-focus fluorescent light 152 passes through sensor aperture mechanism 130 and reaches TDI image sensor 146, while out-of-focus fluorescent light 154 is rejected by the pinholes or slits in sensor aperture mechanism 130. In one example, TDI image sensor 146 is a long linear sensor, such as 3200×64 pixel sensor, for capturing high resolution images of tissue sample 120.

Figure 2:
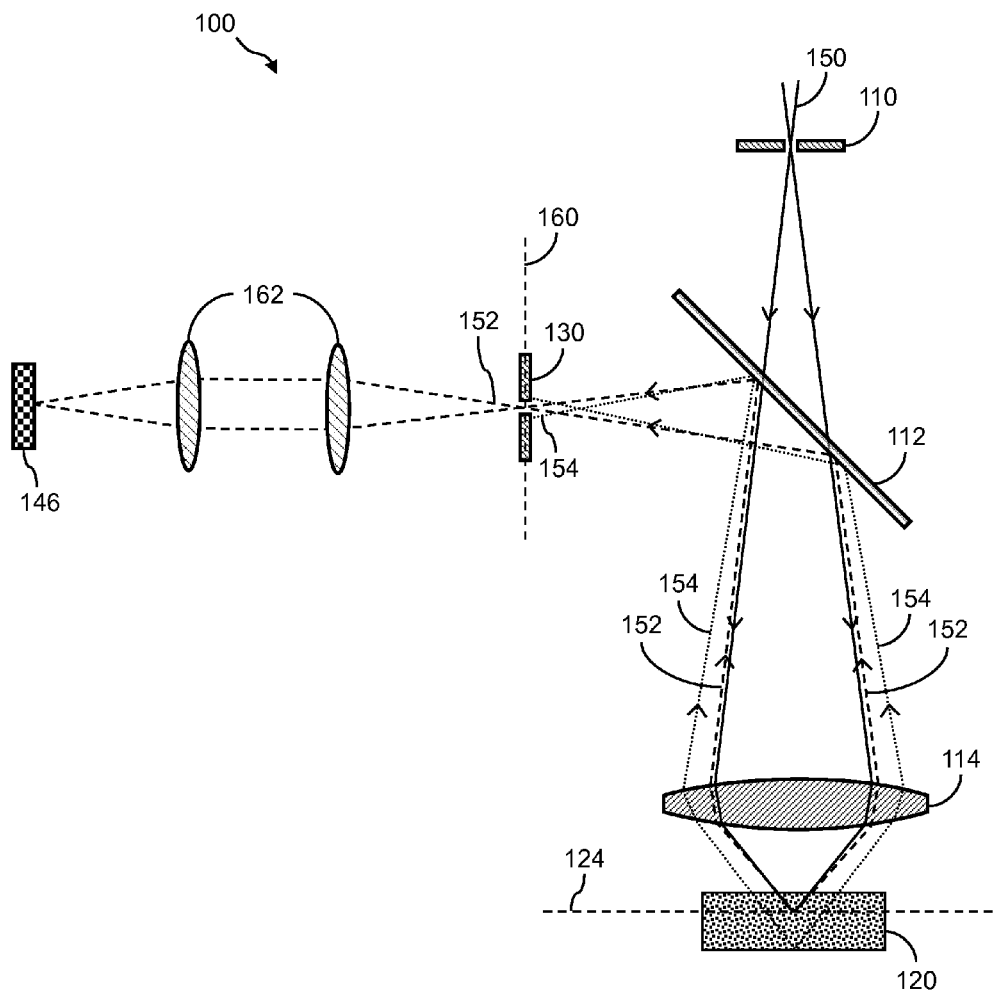
FIG. 2 illustrates another configuration of the confocal imaging system shown in FIG. 1.

FIG. 2 shows another configuration of confocal imaging system 100 in which sensor aperture mechanism 130 is positioned in an intermediate image plane 160 that is conjugating to TDI image sensor 146. In this configuration of confocal imaging system 100, an additional pair of lens 162 is arranged between sensor aperture mechanism 130, which is at intermediate image plane 160, and TDI image sensor 146. More details of examples of sensor aperture mechanism 130 for rejecting the out-of-focus light are shown and described hereinbelow with reference to FIGS. 3, 4A, 4B, 5A, and 5B.

Figure 3:
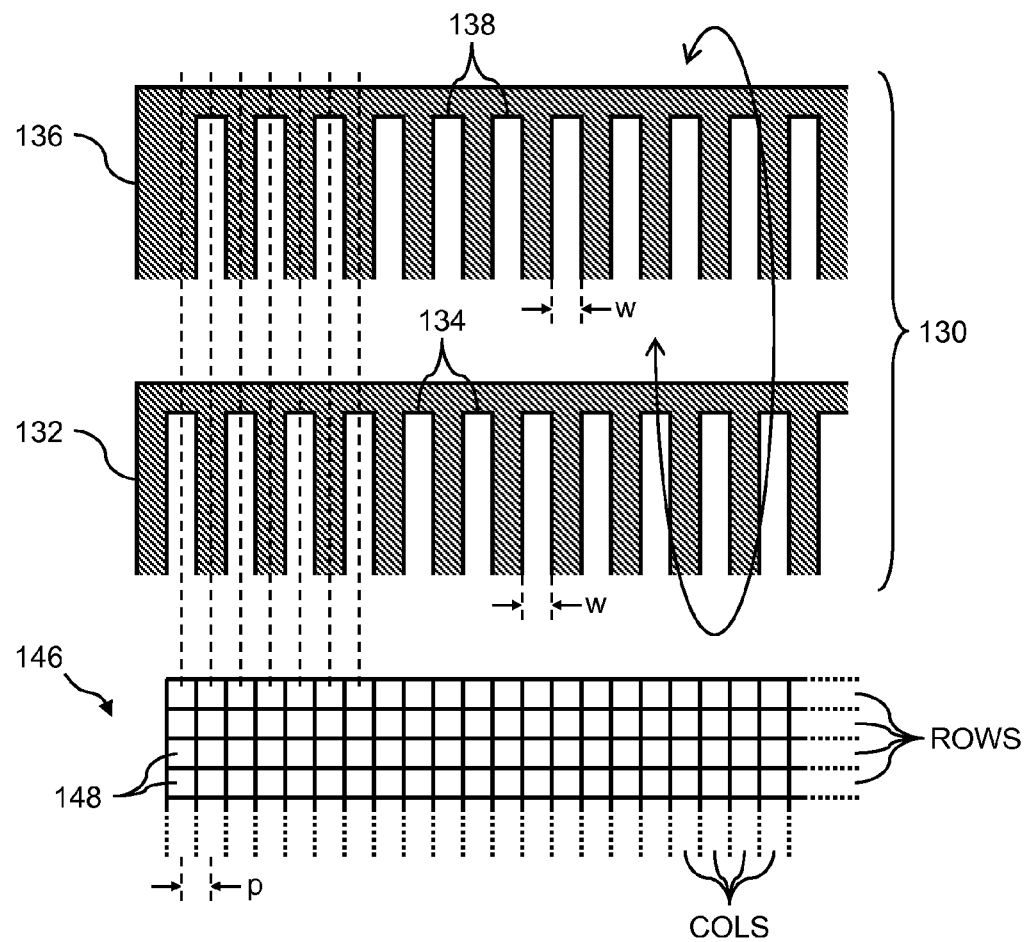
FIG. 3 illustrates a side view of an example of a sensor aperture mechanism of the confocal imaging system shown in FIGS. 1 and 2.

FIG. 3 illustrates a side view of an example of sensor aperture mechanism 130 of confocal imaging system 100 shown in FIGS. 1 and 2. Namely, FIG. 3 shows an example of TDI image sensor 146 that includes a 3200×64 array of pixels 148 (i.e., 3200 columns×64 rows, wherein the first column is column #1). In this example, sensor aperture mechanism 130 comprises two apertures whose positions are switchable—one aperture for the odd columns of TDI image sensor 146 and another aperture for the even columns of TDI image sensor 146. Namely, sensor aperture mechanism 130 comprises a first aperture plate 132 that comprises slits 134 and a second aperture plate 136 that comprises slits 138. Aperture plate 132 and aperture plate 136 are formed of a material that is not optically transparent to the wavelengths present in confocal imaging system 100. For example, aperture plate 132 and aperture plate 136 can be formed of a glass substrate coated by patterned opaque layers, such as chrome. Further, the height and length of aperture plate 132 and aperture plate 136 may depend on the overall size of TDI image sensor 146.

Both aperture plate 132 and aperture plate 136 can be positioned with respect to the columns of pixels 148 of TDI image sensor 146. The positions of aperture plate 132 and aperture plate 136 are mechanically switchable so that only one aperture plate is in front of TDI image sensor 146 at any given time. For example, aperture plate 132 and aperture plate 136 can be switchable in a rotating or shifting fashion under the control of a controller (not shown). Aperture plate 132 is designed so that, when in front of TDI image sensor 146, the positions of slits 134 substantially correspond to the positions of the odd pixel columns of TDI image sensor 146. Namely, aperture plate 132 is open to the odd pixel columns of TDI image sensor 146 and blocks the even columns. By contrast, aperture plate 136 is designed so that, when in front of TDI image sensor 146, the positions of slits 138 substantially correspond to the positions of the even pixel columns of TDI image sensor 146. Namely, aperture plate 136 is open to the even pixel columns of TDI image sensor 146 and blocks the odd columns.

In aperture plate 132 and aperture plate 136, placing a slot corresponding to every other (i.e., every second) pixel column ensures adequate out-of-focus light rejection. Further, sensor aperture mechanism 130 is not limited to two aperture plates only. More than two aperture plates can be used to further improve confocality if needed, but with the tradeoff of reducing the scan speed. For example, sensor aperture mechanism 130 can comprise three aperture plates. The first aperture plate has a slit at the first pixel column and then slits at every third pixel column thereafter. The second aperture plate has a slit at the second pixel column and then slits at every third pixel column thereafter. The third aperture plate has a slit at the third pixel column and then slits at every third pixel column thereafter. Again, the positions of three aperture plates are mechanically switchable so that only one aperture plate is in front of TDI image sensor 146 at any given time.

Slits 134 in aperture plate 132 and slits 138 in aperture plate 136 have a width w. The width w is determined by the size of pixels 148 of TDI image sensor 146. In confocal imaging system 100, the width w of slits 134 and slits 138 can be from about 1 μm to about 12 μm in one example, or is about 9 μm in another example. The spacing between slits 134 in aperture plate 132 and between slits 138 in aperture plate 136 may depend on the pitch p of pixels 148 of TDI image sensor 146. As a non-limiting example, the spacing between slits 134 in aperture plate 132 and between slits 138 in aperture plate 136 may be substantially the same as the pitch p of pixels 148 of TDI image sensor 146. Further, the length of slits 134 in aperture plate 132 and of slits 138 in aperture plate 136 may depend on the overall size of TDI image sensor 146. As a non-limiting example, the length of slits 134 in aperture plate 132 and of slits 138 in aperture plate 136 may be substantially the same as the width of TDI image sensor 146 along a same dimension as the length of the slits 134 and slits 138.

The switch cycle of aperture plate 132 and aperture plate 136 is synchronized to the TDI line scan speed, specifically one switch cycle or an integer number of cycles in a TDI scan readout. In operation, in the first imaging or scanning half-cycle, aperture plate 132 is switched into position in front of TDI image sensor 146 whereby the odd pixel columns of TDI image sensor 146 are open while the even pixel columns are blocked. In this half-cycle, image data of the odd pixel columns of TDI image sensor 146 is captured. Then, in the next imaging or scanning half-cycle, aperture plate 132 is switched out and aperture plate 136 is switched into position in front of TDI image sensor 146 whereby the even pixel columns of TDI image sensor 146 are open while the odd pixel columns are blocked. In this half-cycle, image data of the even pixel columns of TDI image sensor 146 is captured. The motion of aperture plate 132 and aperture plate 136 is synchronized with the high speed TDI imaging process. In one example, aperture plate 132 and aperture plate 136 are switchable at a rate of from about 5 kHz to about 35 kHz.

Figure 4A:
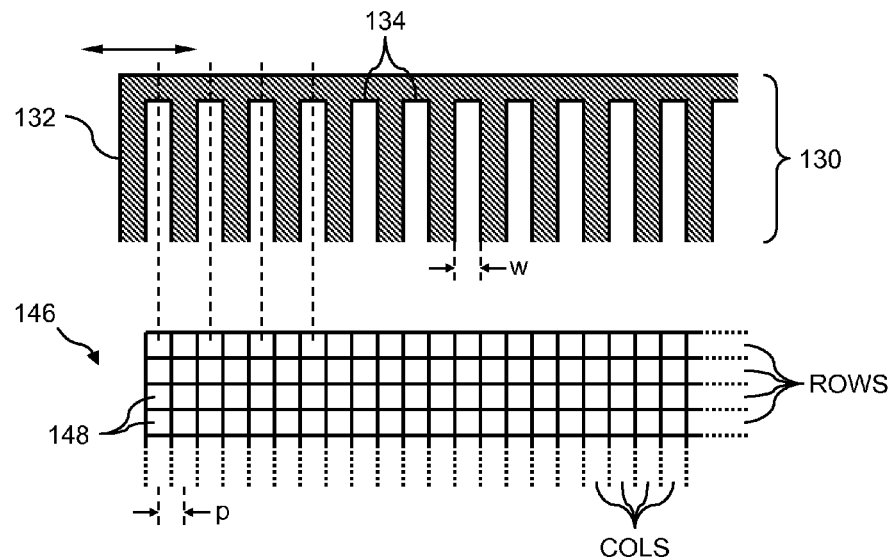
FIGS. 4A and 4B illustrate side views of another example of the sensor aperture mechanism of the confocal imaging system shown in FIGS. 1 and 2.
Figure 4B:
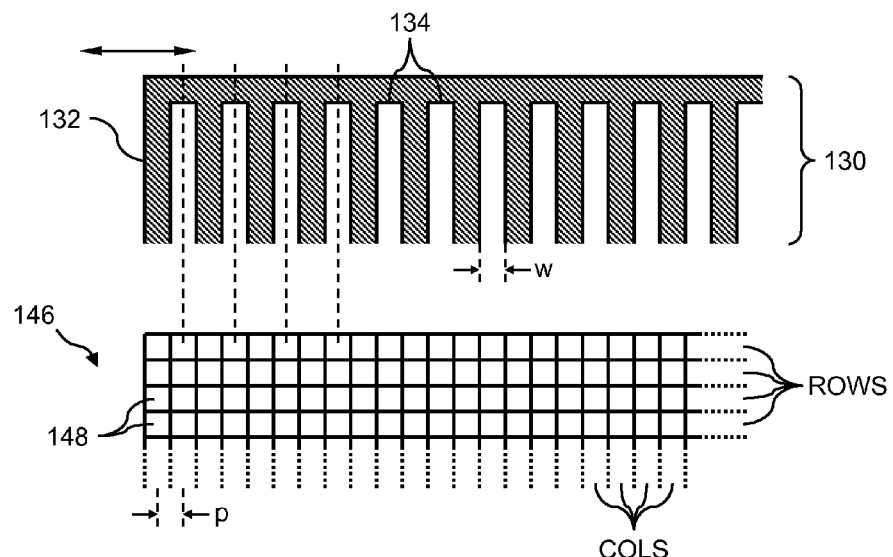

FIGS. 4A and 4B illustrate side views of another example of sensor aperture mechanism 130 of confocal imaging system 100 shown in FIGS. 1 and 2. In this example, only one aperture is used in front of TDI image sensor 146, wherein the one aperture can be shifted side-to-side to alternately allow or block the odd and even pixel columns. In one example, aperture plate 132 as described with referenced to FIG. 3 is provide in front of TDI image sensor 146 and mechanically shifted side-to-side during the imaging or scanning process. FIG. 4A shows aperture plate 132 and slits 134 in a first position with respect to TDI image sensor 146, wherein the odd pixel columns are open and the even pixel columns are blocked. By contrast, FIG. 4B shows aperture plate 132 and slits 134 in a second position with respect to TDI image sensor 146, wherein the even pixel columns are open and the odd pixel columns are blocked.

In operation, in the first imaging or scanning half-cycle, aperture plate 132 is positioned in front of TDI image sensor 146 such that the odd pixel columns are open and the even pixel columns are blocked, as shown in FIG. 4A. In this half-cycle, image data of the odd pixel columns of TDI image sensor 146 is captured. Then, in the next imaging or scanning half-cycle, the position of aperture plate 132 is mechanically shifted in front of TDI image sensor 146 such that the even pixel columns are open and the odd pixel columns are blocked, as shown in FIG. 4B. In this half-cycle, image data of the even pixel columns of TDI image sensor 146 is captured. Again, the motion of aperture plate 132 is synchronized with the high speed TDI imaging process, wherein the switching rate can be from about 5 kHz to about 35 kHz.

Figure 5A:
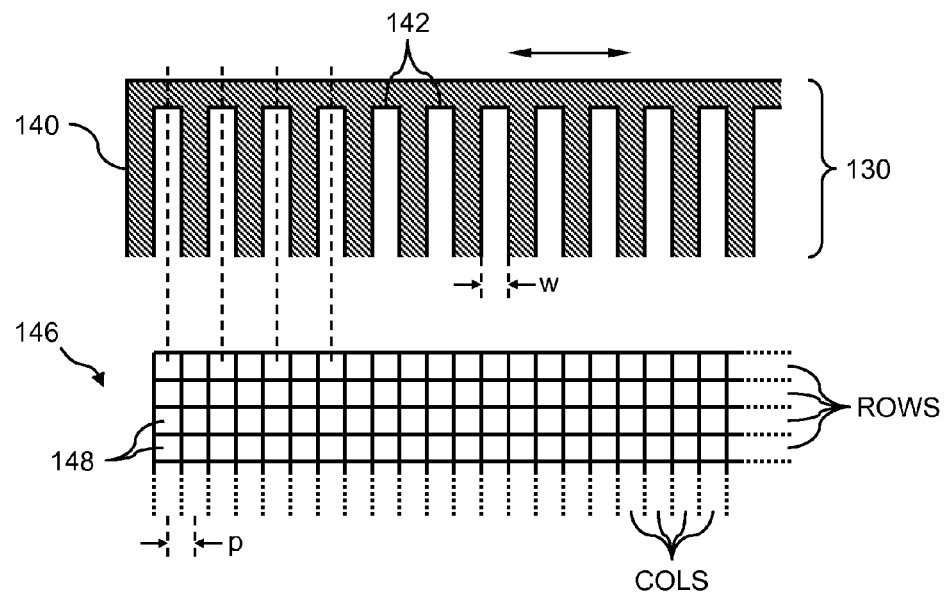
FIGS. 5A and 5B illustrate side views of yet another example of the sensor aperture mechanism of the confocal imaging system shown in FIGS. 1 and 2.
Figure 5B:
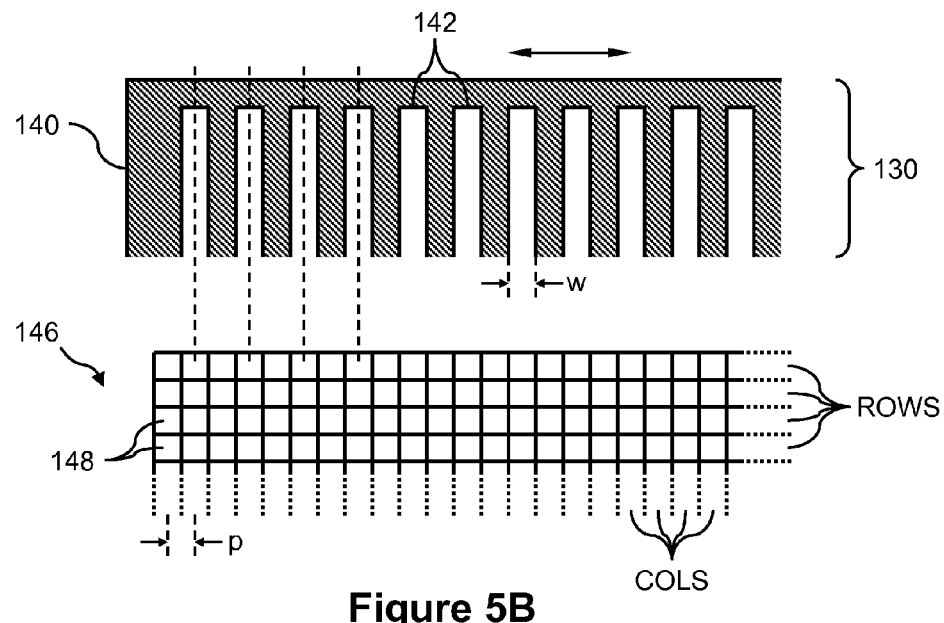

FIGS. 5A and 5B illustrate side views of yet another example of sensor aperture mechanism 130 of confocal imaging system 100 shown in FIGS. 1 and 2. In this example, sensor aperture mechanism 130 is a motionless, electronically controlled spatial light modulator 140. Spatial light modulator 140 can be, for example, a liquid crystal display (LCD)-based device or a micro-electro-mechanical systems (MEMS) mirror device. Windows or slits 142 can be provided electronically in spatial light modulator 140. The size, number, and positions of windows or slits 142 in spatial light modulator 140 are controlled electronically.

In confocal imaging system 100, spatial light modulator 140 can be used in two states. For example, FIG. 5A shows a first state of spatial light modulator 140 in which windows or slits 142 are electronically opened that substantially align with the odd columns of pixels 148 of TDI image sensor 146. By contrast, FIG. 5B shows a second state of spatial light modulator 140 in which windows or slits 142 are electronically opened that substantially align with the even columns of pixels 148 of TDI image sensor 146. The switching frequency of spatial light modulator 140 is synchronized with the high speed TDI imaging process. In one example, the switching frequency of spatial light modulator 140 is from about 5 kHz to about 35 kHz. In confocal imaging system 100, spatial light modulator 140 is not limited to two states, two or more states are possible.

Focus Tracking Mechanisms in an Imaging Process

Certain embodiments of the invention provide structures that comprise focus tracking features that can be used to maintain focus during imaging as described hereinbelow with reference to FIGS. 6A, 6B, 7, 8, and 9. For example, the presently disclosed focus tracking mechanisms are suitable for assisting in laser-based focusing techniques.

Figure 6A:
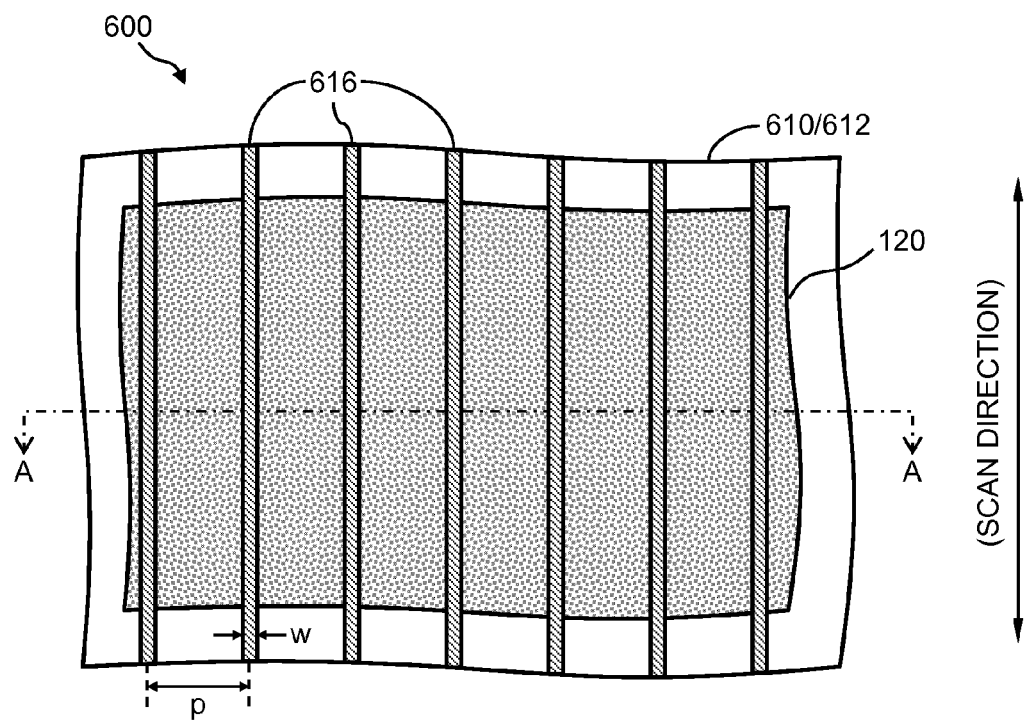
FIGS. 6A and 6B illustrate a plan view and a cross-sectional view, respectively, of an example of a structure comprising focusing strips for improved focus tracking in an imaging process.
Figure 6B:
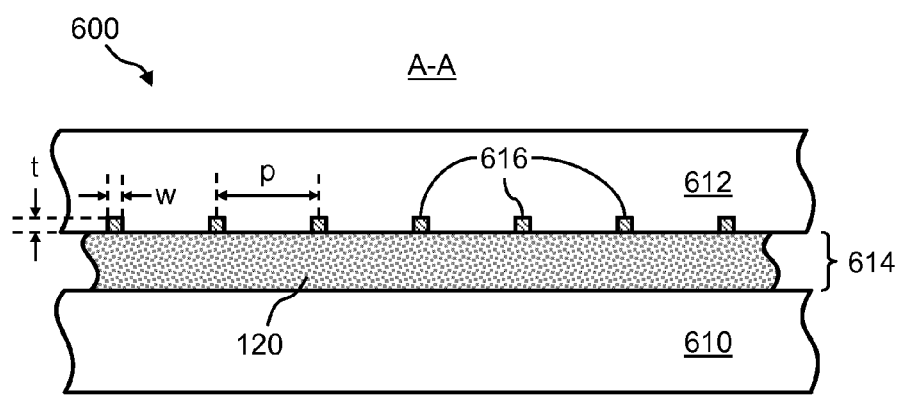

FIGS. 6A and 6B illustrate a plan view and a cross-sectional view, respectively, of an example of a structure 600 comprising focusing strips for improved focus tracking in an imaging process. In this example, structure 600 comprises a bottom substrate 610 and a top substrate 612 that are arranged with a gap 614 therebetween. Tissue sample 120 can be placed on either bottom substrate 610, top substrate 612, or both. Bottom substrate 610 and top substrate 612 can be, for example, glass, plastic, or silicon substrates. A set of focusing strips 616 is provided on the side of top substrate 612 that is facing gap 614. Focusing strips 616 can be formed of, for example, chrome, gold, or other semiconductor—friendly, high-reflection material. Focusing strips 616 can be formed on top substrate 612 using standard photolithography processes. Each of the focusing strips 616 has a thickness t and a width w. In one example, focusing strips 616 have a thickness t of about 50 nm and a width w of about 50 μm. Focusing strips 616 are provided on a pitch p. In one example, the pitch p of focusing strips 616 is about 1100 μm.

Figure 7:
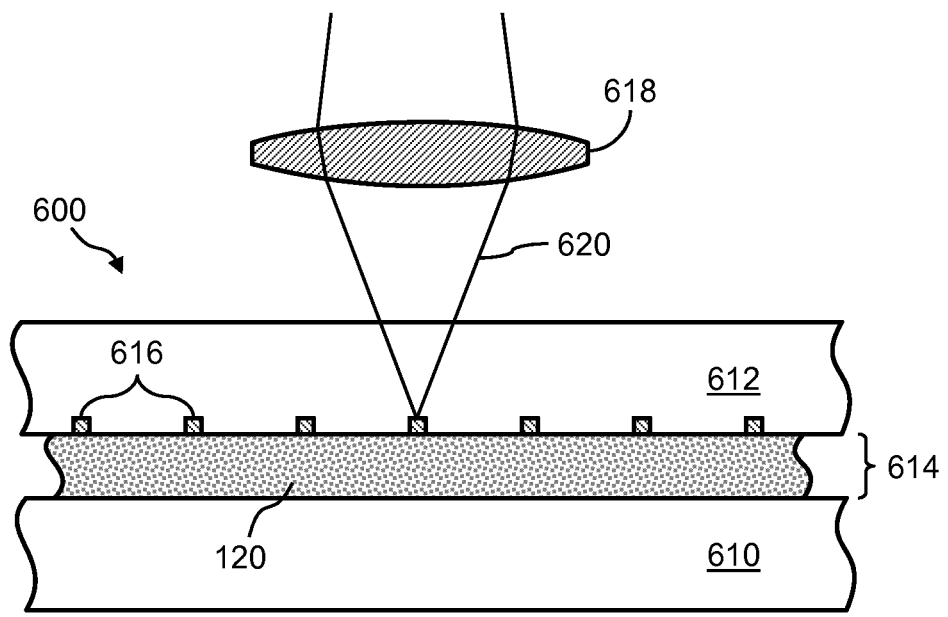
FIG. 7 illustrates a side view of the structure shown in FIGS. 6A and 6B when in use in an imaging process.

Strip shapes are exemplified as fiducials or optical guides in FIG. 6 and elsewhere herein. However, it will be understood that other shapes and designs can be used in addition to or as alternatives for strips. FIG. 7 illustrates a side view of structure 600 shown in FIGS. 6A and 6B when in use in an imaging process. FIG. 7 shows an application in which imaging is allowed through a substrate. FIG. 7 shows structure 600 in relation to a lens 618 and a lens focusing beam 620, wherein lens 618 and lens focusing beam 620 may be a laser-based focusing mechanism. In this example, imaging is performed through top substrate 612 and wherein that the focusing strips 616 are arranged along the scan direction (see FIG. 6A). Focusing strips 616 are used to assist focus tracking, wherein each of the focusing strips 616 has a physical relationship to tissue sample 120. Namely, focusing strips 616 provide a physical feature in substantially the same plane as tissue sample 120 on which lens focusing beam 620 can be focused.

Figure 8:
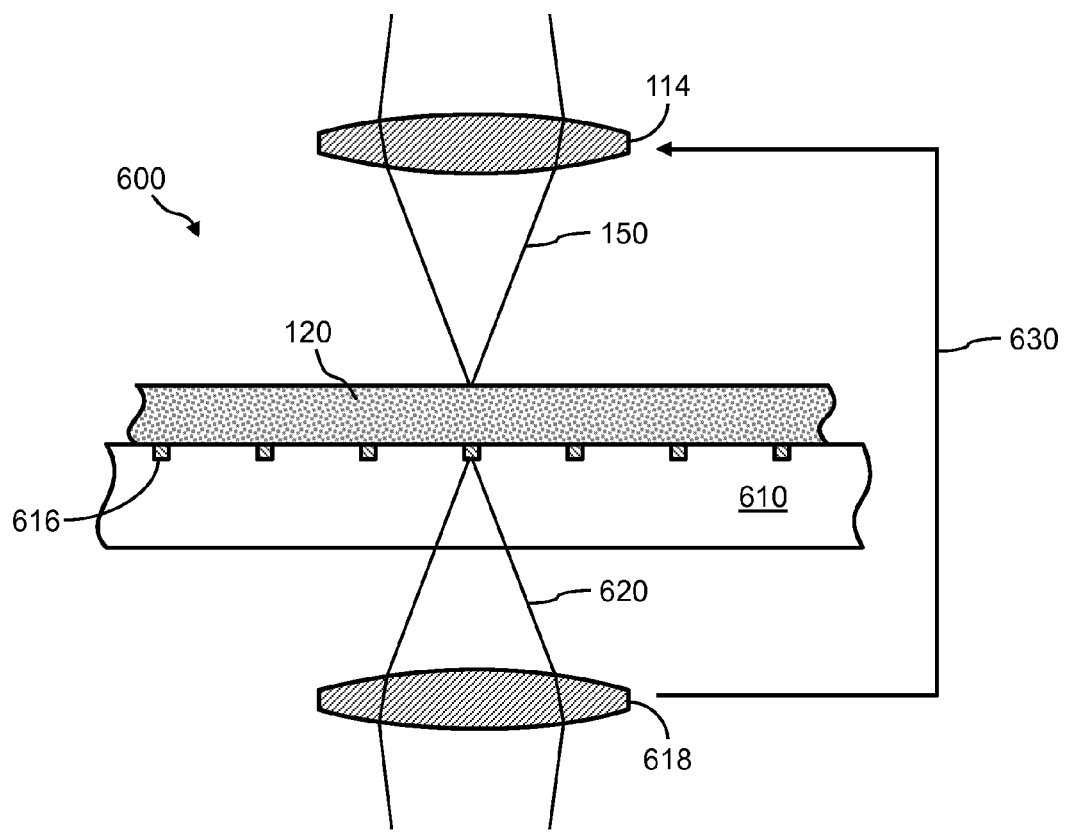
FIG. 8 illustrates a side view of another example of a structure comprising focusing strips for improved focus tracking in an imaging process.

FIG. 8 illustrates a side view of another example of structure 600 comprising focusing strips 616 for improved focus tracking in an imaging process. FIG. 8 shows an application in which imaging may not be allowed through a substrate. In this example, top substrate 612 is omitted and tissue sample 120 is placed on the upper surface of bottom substrate 610. Focusing strips 616 are provided on the upper surface of bottom substrate 610, which is against tissue sample 120. Lens 114 and light source 150, which are used in the fluorescent imaging process, are provided on the exposed side of tissue sample 120. By contrast, lens 618 and laser-based lens focusing beam 620 (as described in FIG. 7) are provided on the bottom substrate 610-side of tissue sample 120.

In this configuration, lens 618 and lens focusing beam 620, which is the laser-based focusing mechanism, uses focusing strips 616 on bottom substrate 610. A feedback loop is provided from the laser-based focusing mechanism to the fluorescent imaging mechanism. Namely, lens 618, lens focusing beam 620, and focusing strips 616 are used to generate a focus error signal 630 to the fluorescent imaging mechanism (i.e., lens 114 and light source 150). The focus error signal 630 is used to maintain focus during the imaging (or scanning) process.

Figure 9:
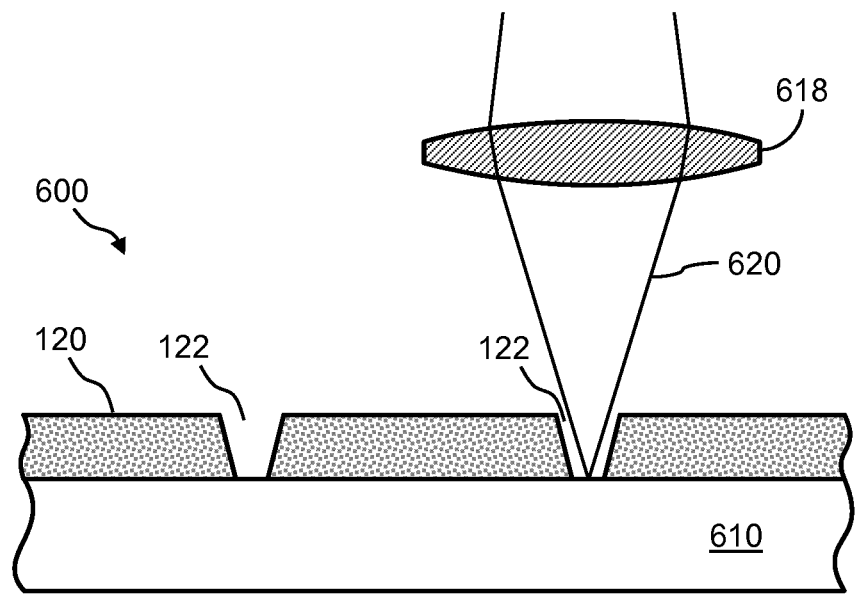
FIG. 9 illustrates a side view of another technique for providing improved focus tracking in an imaging process.

FIG. 9 illustrates a side view of another technique for providing improved focus tracking in an imaging process. In this example, tissue sample 120 is placed atop bottom substrate 610 and strips 122 are cut into tissue sample 120 to expose strips of bottom substrate 610. The strips of exposed substrate can be used as focusing features by, for example, a laser-based focusing mechanism (e.g., lens 618 and lens focusing beam 620).

Flow Cells for Processing Tissue Samples

Currently, the cell culture process is not optimal in a flow cell chamber. Certain embodiments of the invention provide flow cells and methods for processing tissue samples, as described hereinbelow with reference to FIGS. 10A through 17B.

In particular embodiments, advantageous features of a flow cell for use in processing tissues include, but are not necessarily limited to, one or more of the following (1) at least temporary access of a surface of the flow cell that allows a tissue sample to be placed thereon, (2) convenient assembly of flow cell components to at least partially enclose the tissue sample in a fluidic chamber that allows fluids to come into contact with the tissue sample and that the allows formation of a detection zone for observation of the tissue sample, and (c) convenient disassembly to allow a tissue sample to be removed for subsequent analysis (e.g. of the intact tissue or an intact portion thereof) or for re-use of the flow cell. In particular embodiments, the integrity of the flow cell will be substantially the same following disassembly and reassembly. In some embodiments, tools need not be used for assembly or disassembly. However, in some cases hand tools can be provided for convenience and power tools need not be used.

Figure 10A:
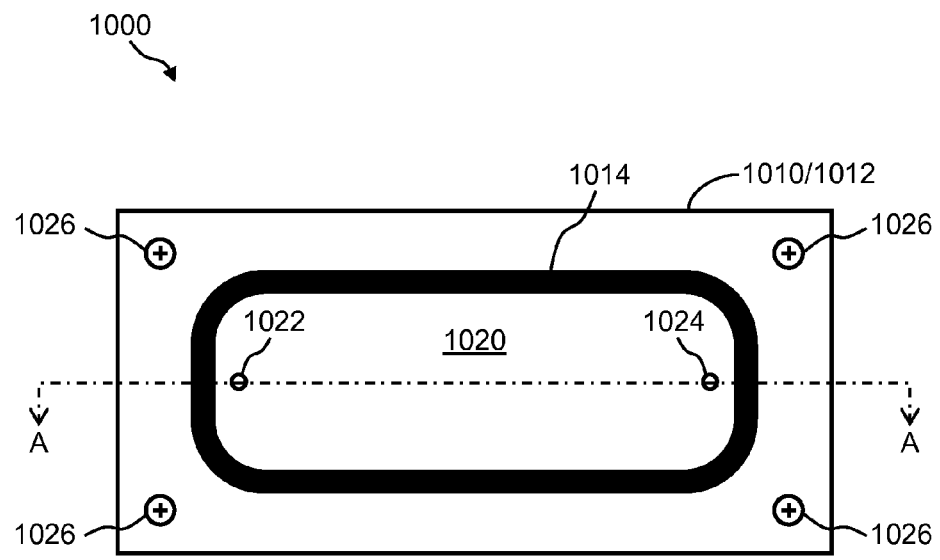
FIGS. 10A and 10B illustrate a plan view and a cross-sectional view, respectively, of an example of a flow cell for holding and processing a tissue sample.
Figure 10B:
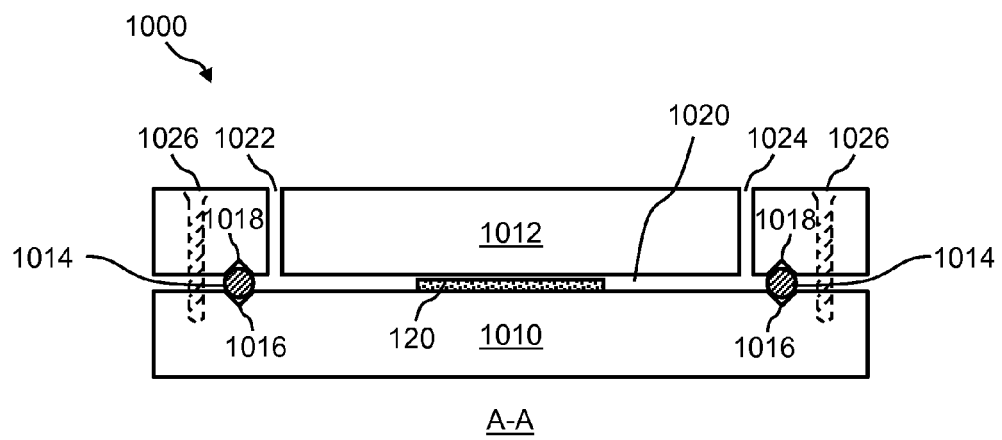

FIGS. 10A and 10B illustrate a plan view and a cross-sectional view, respectively, of an example of a flow cell 1000 for holding a tissue sample and performing any of a variety of types of reaction chemistry, such as SBS chemistry. In this example, flow cell 1000 comprises a bottom substrate 1010 and a top substrate 1012 that are coupled together using an O-ring 1014. O-ring 1014 can be formed of, for example, viton, silicone, or any other materials having process compatibility. Namely, bottom substrate 1010 has a groove 1016 and top substrate 1012 has a groove 1018 for receiving O-ring 1014. When assembled, O-ring 1014 is fitted into groove 1016 of bottom substrate 1010 and groove 1018 of top substrate 1012 and sandwiched between bottom substrate 1010 and top substrate 1012. O-ring 1014 is sized such that when bottom substrate 1010, top substrate 1012, and O-ring 1014 are assembled together there is a space or gap between bottom substrate 1010 and top substrate 1012. In this space or gap, O-ring 1014 defines a reaction chamber 1020 in flow cell 1000. Further, top substrate 1012 has an inlet 1022 and an outlet 1024 for flowing liquid (e.g., reagents) into and/or through reaction chamber 1020 of flow cell 1000. Additionally, in one example, bottom substrate 1010, top substrate 1012, and O-ring 1014 can be held together using screws 1026. FIG. 10B also shows tissue sample 120 inside reaction chamber 1020 of flow cell 1000.

Figure 11:
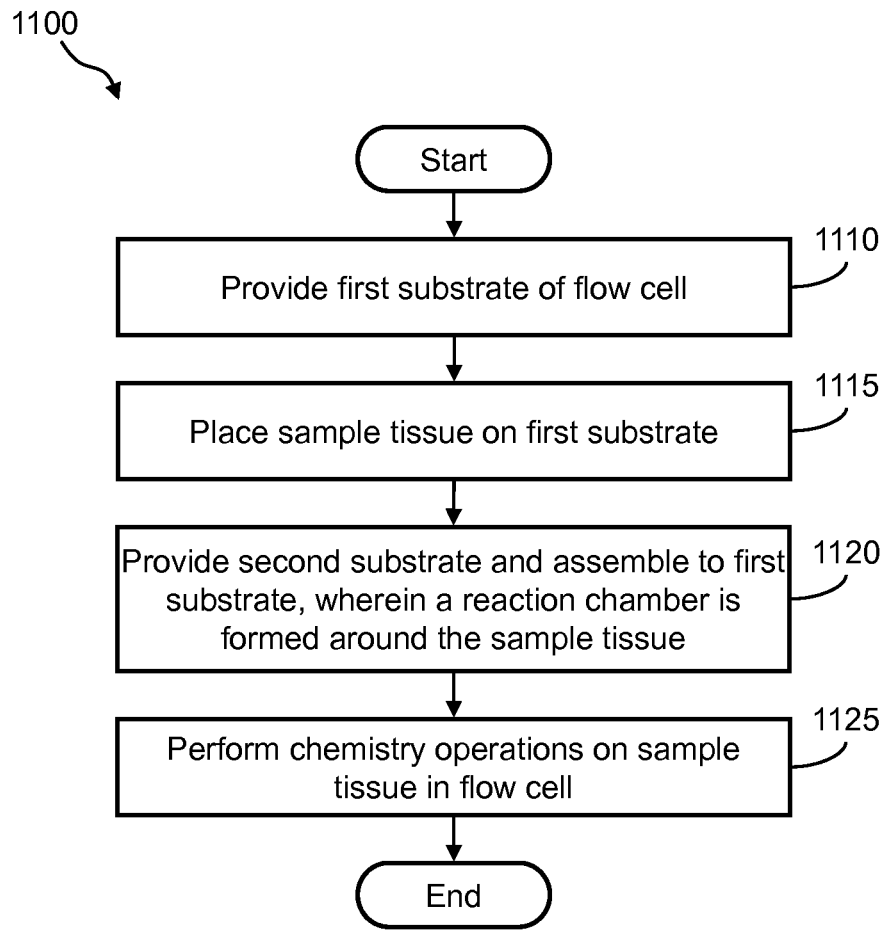
FIG. 11 illustrates a flow diagram of an example of a method of processing a tissue sample using the flow cell shown in FIGS. 10A and 10B.

FIG. 11 illustrates a flow diagram of an example of a method 1100 of processing a tissue sample using flow cell 1000 shown in FIGS. 10A and 10B. Method 1100 may include, but is not limited to, the following steps.

At a step 1110, the first substrate of the flow cell is provided. For example, bottom substrate 1010 of flow cell 1000 is provided.

At a step 1115, the sample tissue is placed on the first substrate. For example, tissue sample 120 is placed on bottom substrate 1010 of flow cell 1000.

At a step 1120, the second substrate is provided and assembled to the first substrate, wherein a reaction chamber is formed around the sample tissue. For example, top substrate 1012 is provided and assembled to bottom substrate 1010 using O-ring 1014 and screws 1026. In so doing, O-ring 1014 defines reaction chamber 1020 around tissue sample 120.

At a step 1125, chemistry operations are performed on the sample tissue. For example, using inlet 1022 and outlet 1024, liquid is flowed into and/or through reaction chamber 1020 of flow cell 1000 and chemistry operations, such as SBS chemistry operations, are performed on tissue sample 120. In this example, the imaging or scanning process of tissue sample 120 can occur through bottom substrate 1010 and/or top substrate 1012.

The method can include imaging steps that accompany a sequencing or other nucleic acid detection technique such as those set forth elsewhere herein. Alternatively, the method can include a step of obtaining a picture, image or other representation of the physical form or structure of the tissue sample. This representation can be obtained via light field, fluorescence or other microscopic techniques and can optionally be aided by the use of dyes or labels. Comparison of this representation with spatially resolved nucleic acid detection results can be used to localize genetic information with recognizable features of a tissue. Exemplary methods for spatial detection of nucleic acids that can be modified for use in the apparatus and methods set forth herein are described in US Pat. App. Pub. No. 2014/0066318 A1 and PCT App. Pub. No. WO 2014/060483 A1, each of which is incorporated herein by reference.

Figure 12A:
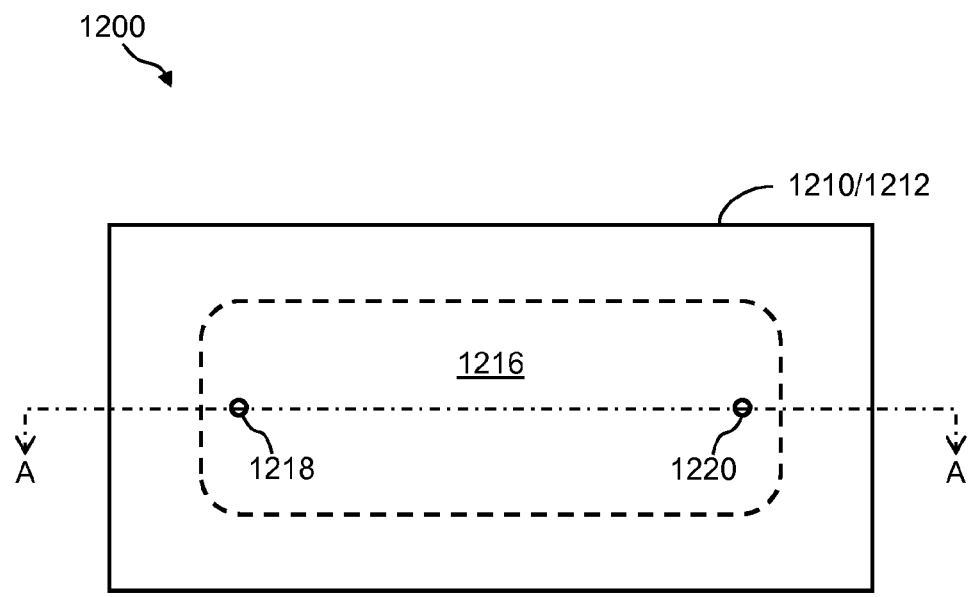
FIGS. 12A and 12B illustrate a plan view and a cross-sectional view, respectively, of another example of a flow cell for holding and processing a tissue sample.
Figure 12B:
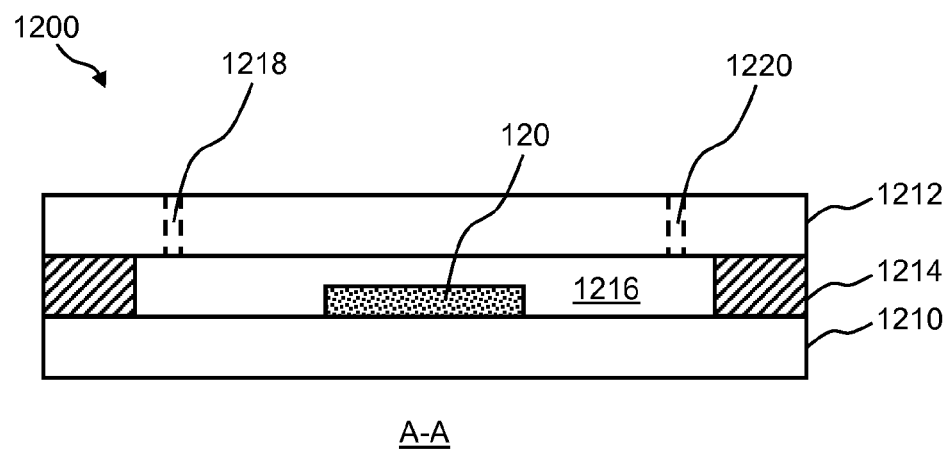
Figure 13A:
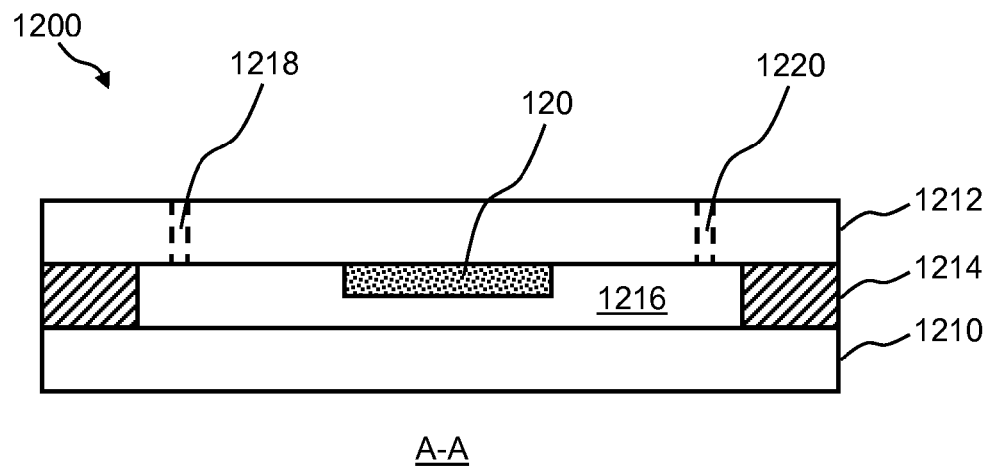
FIGS. 13A and 13B illustrate other side views of the flow cell shown in FIGS. 12A and 12B and showing the tissue sample in different locations in the sequencing chamber.
Figure 13B:
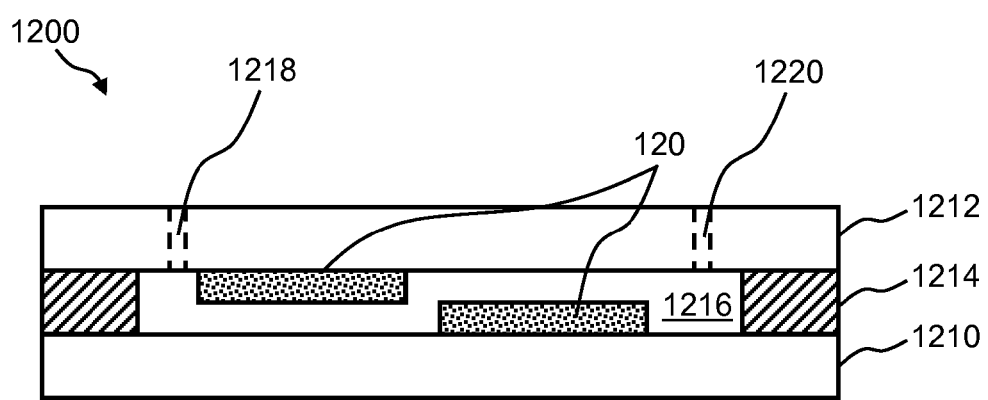
Figure 14A:
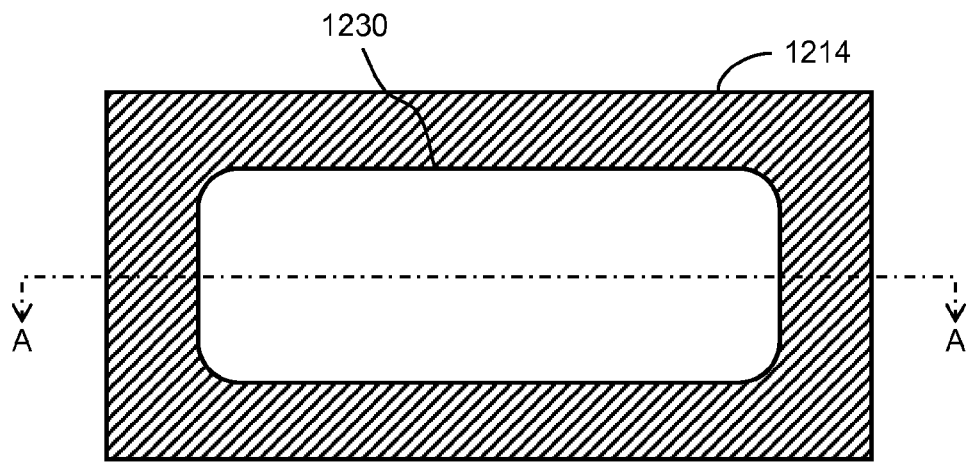
FIGS. 14A and 14B illustrate a plan view and a cross-sectional view, respectively, of an example of the adhesive-portion of the flow cell shown in FIGS. 12A and 12B.
Figure 14B:
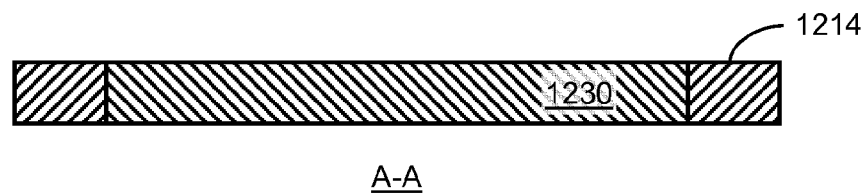

FIGS. 12A and 12B illustrate a plan view and a cross-sectional view, respectively, of another example of a flow cell 1200 for holding a tissue sample and performing any type of reaction chemistry, such as SBS chemistry. In this example, flow cell 1200 comprises a bottom substrate 1210 and a top substrate 1212. Bottom substrate 1210 and top substrate 1212 are bonded together using an adhesive layer 1214 that is sandwiched there between. An opening is provided in adhesive layer 1214, thereby forming a reaction chamber 1216 in flow cell 1200, more details of which are shown in FIGS. 14A and 14B. Further, an inlet 1218 and an outlet 1220 are provided in top substrate 1212. Inlet 1218 and outlet 1220 are used to flow liquid (e.g., reagents) into and/or through reaction chamber 1216 in flow cell 1200.

Adhesive layer 1214 is used to couple together bottom substrate 1210 and top substrate 1212. In one example, adhesive layer 1214 is a layer of two-side tape, such as ultraviolet (UV)-cured two-sided tape.

Inside reaction chamber 1216 of flow cell 1200, a tissue sample can be placed on the top, bottom, or both substrates. For example, FIG. 12B shows tissue sample 120 inside reaction chamber 1216 and on bottom substrate 1210. In another example and referring now to FIG. 13A, tissue sample 120 inside reaction chamber 1216 is on top substrate 1212. In yet another example and referring now to FIG. 13B, inside reaction chamber 1216 there is a first tissue sample 120 is on bottom substrate 1210 and a second tissue sample 120 on top substrate 1212.

Referring now to FIGS. 14A and 14B is a plan view and a cross-sectional view, respectively, of an example of adhesive layer 1214, which is the adhesive-portion of flow cell 1200 shown in FIGS. 12A and 12B. Namely, FIGS. 14A and 14B show an opening 1230 in adhesive layer 1214, which is used to form reaction chamber 1216 of flow cell 1200. In one example, the thickness of adhesive layer 1214 is about 100 μm.

Figure 15:
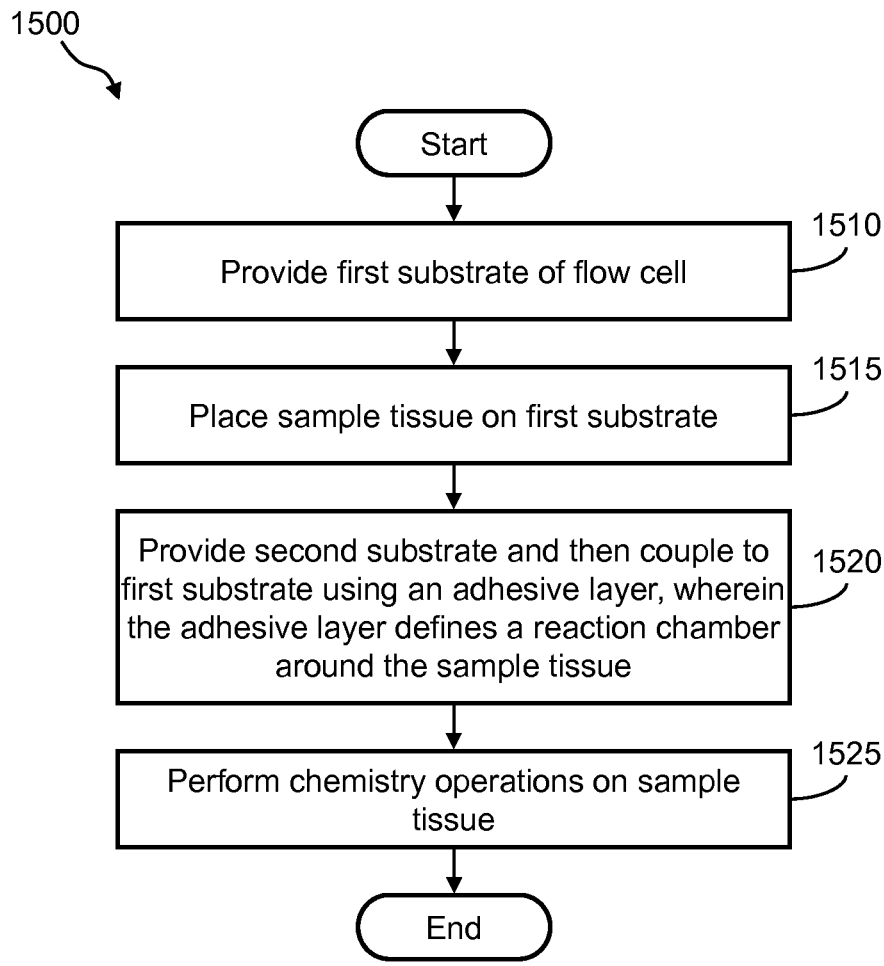
FIG. 15 illustrates a flow diagram of an example of a method of processing a tissue sample using the flow cell shown in FIGS. 12A and 12B.

FIG. 15 illustrates a flow diagram of an example of a method 1500 of processing a tissue sample using flow cell 1200 shown in FIGS. 12A and 12B. Method 1500 may include, but is not limited to, the following steps.

At a step 1510, the first substrate of the flow cell is provided. For example, bottom substrate 1210 of flow cell 1200 is provided.

At a step 1515, the sample tissue is placed on the first substrate. For example, tissue sample 120 is placed on bottom substrate 1210 of flow cell 1200.

At a step 1520, a second substrate is provided and then coupled to the first substrate using an adhesive layer, wherein the adhesive layer defines a reaction chamber around the sample tissue. For example, top substrate 1212 is provided and then coupled to bottom substrate 1210 using adhesive layer 1214 (e.g., UV-cured two-sided tape), wherein the opening 1230 in adhesive layer 1214 forms reaction chamber 1216 around tissue sample 120. In the case of UV-cured two-sided tape, a UV cure operation can occur in this step to form the bonds between adhesive layer 1214 and bottom substrate 1210 and top substrate 1212.

At a step 1525, chemistry operations are performed on the sample tissue. For example, using inlet 1218 and outlet 1220, liquid is flowed into and/or through reaction chamber 1216 of flow cell 1200 and chemistry operations, such as SBS chemistry operations, are performed on tissue sample 120. In this example, the imaging or scanning process of tissue sample 120 can occur through bottom substrate 1210 and/or top substrate 1212. Again, imaging can be carried out as part of a nucleic acid detection technique and/or to determine the shape or form of the tissue sample.

Figure 16A:
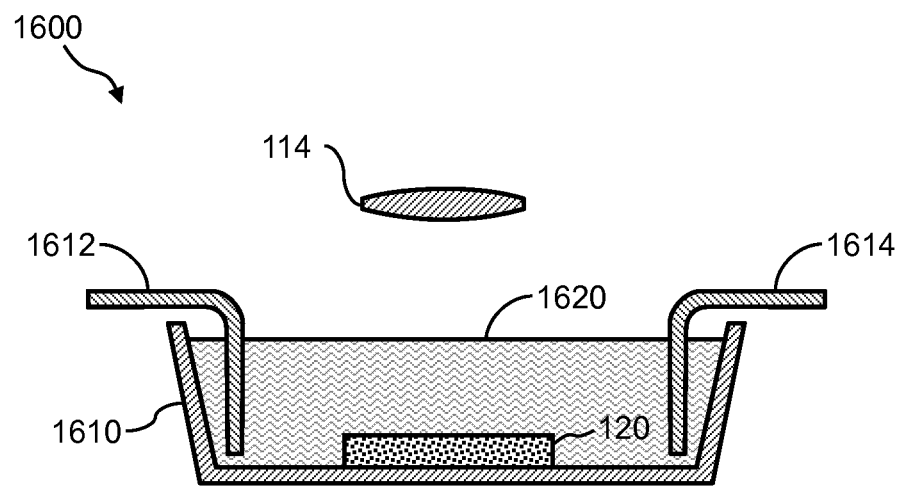
FIGS. 16A and 16B illustrate side views of an example of a flow cell that uses an open container for holding a tissue sample and an example of a process of "dry" imaging the tissue sample therein.
Figure 16B:
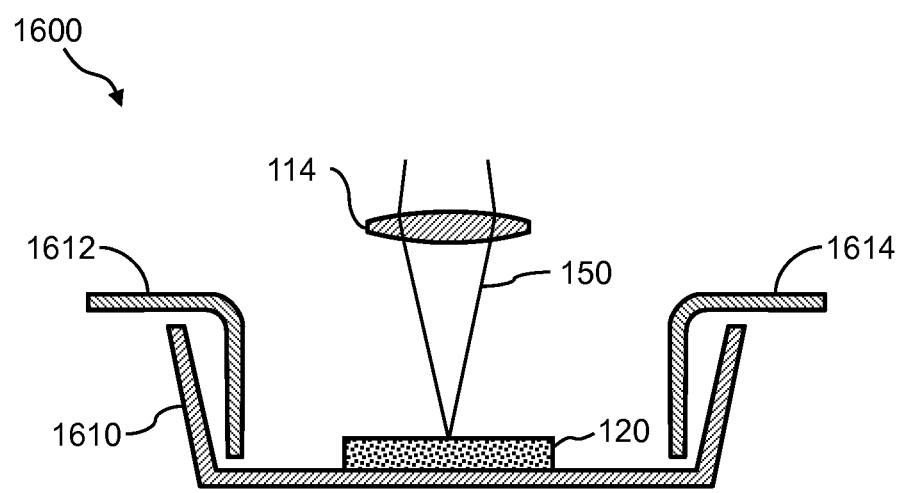

FIGS. 16A and 16B illustrate side views of an example of a flow cell 1600 that uses an open container for holding a tissue sample and an example of a process of "dry" imaging the tissue sample therein. In this example, flow cell 1600 comprises an open container 1610. Two or more tubes are provided with respect to open container 1610, which serve as inlet(s) and/or outlet(s) thereof. For example, a tube 1612 and a tube 1614 are provided with respect to open container 1610, wherein one end of tube 1612 and one end of tube 1614 is inside open container 1610. Namely, tube 1612 and tube 1614 are used to flow liquid 1620 (e.g., reagents) into and/or through open container 1610. Additionally, FIGS. 16A and 16B show tissue sample 120 inside open container 1610.

In the process of imaging tissue sample 120 in open container 1610, FIG. 16A shows open container 1610 filled with liquid 1620 and chemistry operations occurring on tissue sample 120. Referring now to FIG. 16B, upon completion of the chemistry operations, using tube 1612 and tube 1614, open container 1610 is substantially drained of liquid 1620 and then the imaging or scanning process of tissue sample 120 occurs through an air gap in the absence of liquid 1620. Namely, FIG. 16B shows a substantially "dry" imaging process. Some minimal amount of moisture level may be maintained in open container 1610 such that tissue sample 120 may not be completely dry.

Figure 17A:
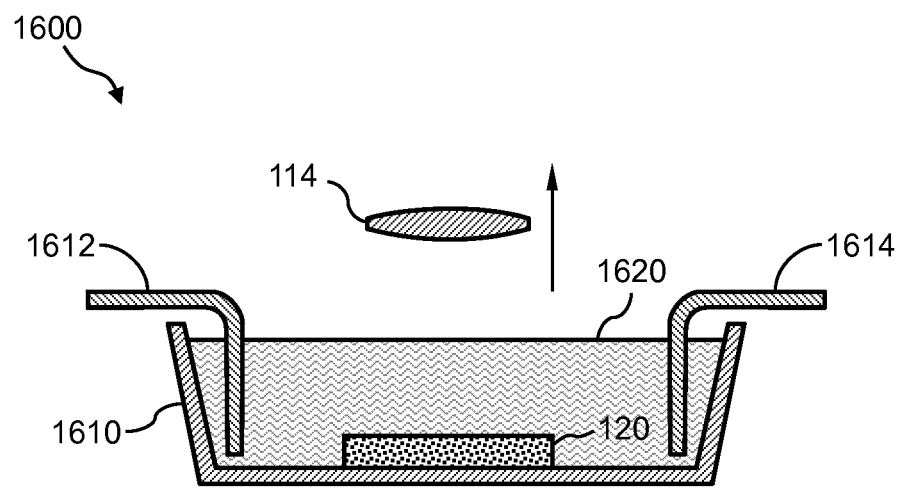
FIGS. 17A and 17B illustrate side views of the flow cell shown in FIGS. 16A and 16B and a liquid-immersion process of imaging the tissue sample therein.
Figure 17B:
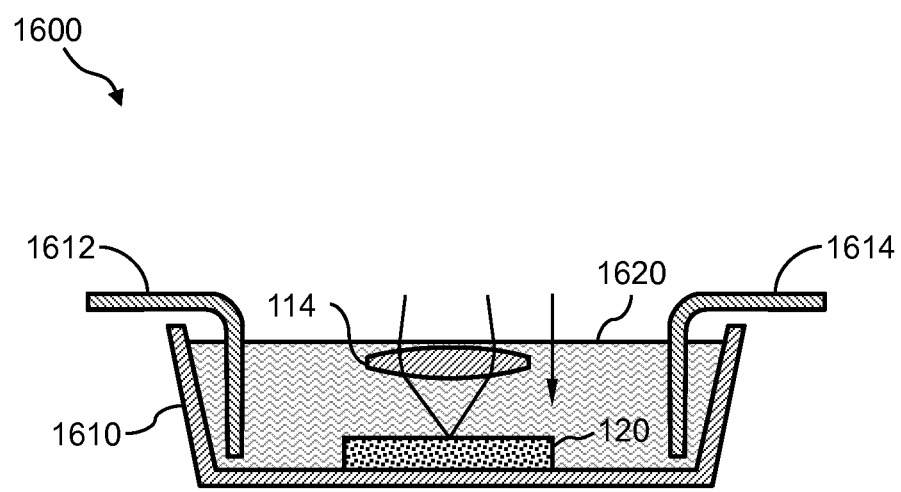

Referring now to FIGS. 17A and 17B, a liquid-immersion imaging process can be used. For example, FIG. 17A shows open container 1610 filled with liquid 1620 and chemistry operations occurring on tissue sample 120. The imaging lens (e.g., lens 114) is positioned outside of open container 1610 and not immersed in liquid 1620. Upon completion of the chemistry operations, FIG. 17B shows open container 1610 still filled with liquid 1620 and the imaging lens (e.g., lens 114) is lowered into open container 1610 and immersed in liquid 1620. In this example, the imaging or scanning process of tissue sample 120 occurs without an air gap. Without the air gap, there can be improved resolution and S/N ratio, as well it can be easier to focus.

In the foregoing detailed description with reference to FIGS. 1 through 17B, the terms "top," "bottom," "over," "under," and "on" are used throughout the description with reference to the relative positions of components of the structures and/or flow cells, such as relative positions of top and bottom substrates of a flow cell. It will be appreciated that the structures and/or flow cells are functional regardless of their orientation in space.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

In the present application, conditional language such as, among others, "can," "could," "might," or "may," unless specifically stated otherwise or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements, and/or steps are included or are to be performed in any particular embodiment. Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

Various modifications of the above described embodiments will be readily apparent, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A confocal time delay and integration (TDI) line scan imaging system comprising:
    a light source;
    an optical beam splitter;
    a lens;
    a TDI image sensor; and
    a TDI image sensor aperture mechanism, the TDI image sensor aperture mechanism comprising an aperture plate comprising a material that is not optically transparent to wavelengths detected by the TDI image sensor, the aperture plate comprising a plurality of slits to focus light on a plurality of pixel columns of the TDI image sensor, wherein positions of the plurality of slits substantially correspond to positions of the plurality of pixel columns of the TDI image sensor.

2. The confocal TDI line scan imaging system of claim 1, wherein the TDI image sensor aperture mechanism is positioned in an optically conjugate plane in front of the TDI image sensor.

3. The confocal TDI line scan imaging system of claim 1, wherein the TDI image sensor comprises a long linear sensor.

4. The confocal TDI line scan imaging system of claim 1, wherein the TDI image sensor aperture mechanism is positioned in an intermediate image plane conjugating to the TDI image sensor.

5. The confocal TDI line scan imaging system of claim 1, wherein the TDI image sensor aperture mechanism comprises a first set of apertures and a second set of apertures having switchable positions.

6. The confocal TDI line scan imaging system of claim 5, wherein the first set of apertures is positioned with respect to a corresponding first set of pixels on the TDI image sensor and the second set of apertures is positioned with respect to a corresponding second set of pixels on the TDI image sensor.

7. The confocal TDI line scan imaging system of claim 1, wherein the TDI image sensor aperture mechanism further comprises a second aperture plate comprising a material that is not optically transparent to wavelengths detected by the TDI image sensor, the second aperture plate comprising a plurality of slits, wherein the first aperture plate and the second aperture plate are switchable during imaging of a sample.

8. The confocal TDI line scan imaging system of claim 7, wherein the plurality of slits of the first aperture plate substantially correspond to even numbered pixel columns of the TDI image sensor and wherein the plurality of slits of the second aperture plate substantially correspond to odd numbered pixel columns of the TDI image sensor, such that as switching occurs, only one aperture plate is in front of the TDI image sensor at any given time.

9. The confocal TDI line scan imaging system of claim 1, wherein a controller synchronizes a switch cycle of the aperture plate to a TDI line scan speed of one switch cycle or an integer number of cycles in a TDI scan readout.

10. The confocal TDI line scan imaging system of claim 9, wherein in a first imaging half-cycle, the aperture plate is switched into position in front of the TDI image sensor whereby odd pixel columns of the TDI image sensor are open and even pixel columns of the TDI image sensor are blocked.

11. The confocal TDI line scan imaging system of claim 9, wherein in a second imaging half-cycle, a second aperture plate is switched into position in front of the TDI image sensor whereby even pixel columns of the TDI image sensor are open and odd pixel columns of the TDI image sensor are blocked.

12. The confocal TDI line scan imaging system of claim 1, further comprising: a substrate having one or more focus tracking mechanisms provided thereon.

13. The confocal TDI line scan imaging system of claim 12, wherein the focus tracking mechanism comprises a focusing strip.

14. The confocal TDI line scan imaging system of claim 13, wherein the focusing strip comprises a high-reflection material.

15. The confocal TDI line scan imaging system of claim 12, wherein the focus tracking mechanism comprises a groove cut into a tissue sample.

16. The confocal TDI line scan imaging system of claim 15, wherein the groove exposes the surface of a bottom substrate.

17. The confocal TDI line scan imaging system of claim 12, the substrate having an exposed side comprising a tissue sample disposed in direct contact with the focus tracking mechanism on the same surface of the substrate.

18. The confocal TDI line scan imaging system of claim 17, wherein the substrate further comprising a laser-based focusing mechanism provided on the opposite side of the exposed side.

19. The confocal TDI line scan imaging system of claim 1, further comprising a flow cell, the flow cell comprising a first substrate upon which a tissue sample to be imaged can be disposed.

20. The confocal TDI line scan imaging system of claim 19, further comprising a second substrate, the first and second substrate separated by a gap, whereby the first substrate, second substrate and gap define a reaction chamber.

21. The confocal TDI line scan imaging system of claim 20, wherein the flow cell comprises an inlet and an outlet for flowing liquid into and through the reaction chamber.

22. A method of processing a tissue sample comprising:
    providing a first substrate of a flow cell;
    placing a sample tissue on the first substrate;
    providing a second substrate and assembling the second substrate to the first substrate, wherein a reaction chamber is formed around the sample tissue; and
    performing imaging of the sample tissue in the reaction chamber.

23. The method of claim 22, wherein the reaction chamber comprises a spacer disposed between the first and second substrates.

24. The method of claim 23, wherein the spacer comprises an O-ring.

25. The method of claim 23, wherein the spacer comprises an adhesive layer.

26. The method of claim 22, wherein the flow cell comprises liquid and an imaging lens is immersed in the liquid.

27. The method of claim 26, wherein the flow cell is substantially drained of liquid and the imaging lens is not immersed in the liquid.

* * * * *